US00PP09832P

United States Patent [19]

van der Knaap

[11] Patent Number: Plant 9,832

[45] Date of Patent: Mar. 18, 1997

[54] FICUS VARIETY NAMED 'BUSHY KING'

[75] Inventor: Wim van der Knaap, De Kwakel, Netherlands

[73] Assignee: K. and W. v.d. Knapp, Netherlands

[21] Appl. No.: 550,016

[22] Filed: Oct. 30, 1995

[51] Int. Cl.[6] ..... A01H 5/00

[52] U.S. Cl. ..... Plt./88.9

[58] Field of Search ..... Plt./88.9

[56] References Cited

U.S. PATENT DOCUMENTS

P.P. 6,460 12/1988 Simoens ..... Plt./88.9

P.P. 8,902 9/1994 Denis ..... Plt./88.9

*Primary Examiner*—James R. Feyrer

*Attorney, Agent, or Firm*—Christie, Parker & Hale, LLP

[57] ABSTRACT

A variety of *Ficus benjamina* having small leaves, short internode length and a bushy appearance.

1 Drawing Sheet

BACKGROUND OF THE INVENTION

The present invention relates to a new and distinct cultivar discovered as a mutation in a controlled planting of *Ficus benjamina* 'Golden King' in a greenhouse in The Netherlands. The varietal denomination of the new cultivar is 'Bushy King'.

SUMMARY OF THE INVENTION

The new variety is a mutation of the variety *Ficus benjamina* 'Golden King.' *Ficus benjamina* 'Bushy King' has been asexually reproduced by rooted cuttings in De Kwakel, The Netherlands. Asexual reproduction through succeeding generations has established that the combination of characteristics as herein disclosed for the new cultivar are firmly fixed and retained through successive generations of asexual reproduction.

COMPARISON WITH PARENT AND OTHER VARIETIES

The new variety if distinguished by its compact growth habit. *Ficus benjamina* 'Bushy King' differs significantly in appearance from its parent *Ficus benjamina* 'Golden King' in that the parent has larger leaves (about 30 mm×70 mm) and longer internode spacing (nominally about 28 mm). The leaves of 'Bushy King' are from 40 mm long×22 mm wide to 66 mm long×30 mm wide. Whereas 'Golden King' has about 5 mature leaves per 110 mm of stem, 'Bushy King' has nominally about 17 leaves per 110 mm of stem.

BRIEF DESCRIPTION OF THE ILLUSTRATION

The accompanying illustration shows a specimen of the new cultivar true to color as is reasonably possible to make in an illustration of this character, showing its compact, bushy growth habit as a 14-month old plant comprised of a single rooted cutting in a 35 cm pot approximately 120 cm tall.

DESCRIPTION OF THE NEW VARIETY

'Bushy King' has not been observed under all possible environmental conditions. The phenotypic expression may vary with variations in environment such as temperature, light intensity, day length, fertilizer rates and other cultural conditions.

The following observations and descriptions are of plants grown in under glass in the Netherlands. In this description, color references are to The Royal Horticultural Society Colour Chart (R.H.S.C.C.). The terminology used in the color descriptions herein refers to plate numbers in this color chart.

Classification:

*Botanical.*—*Ficus benjamina* 'Bushy King'.

Parentage: Mutation of *Ficus benjamina* 'Golden King'.

Propagation: By vegetative cuttings, air layering and other known asexual reproduction techniques.

PLANT

A. Form: Compact, upright, vigorously branching, woody ornamental.

B. Growth: Main stem irregularly by branching with side branching at sharp angles, about 60°, to the main stem.

1. *Height attained.*—About 1.33 meters grown under glass, maintained by pruning for commercial purposes.

C. Foliage:

1. *Form.*—Ovate-elliptical with aristate leaf tip.
2. *Size.*—About 46 mm long by about 22 mm wide to about 65 mm long by about 33 mm wide.
3. *Quantity.*—Multiple, numerous, alternating.
4. *Margin.*—Smooth (entire), slightly undulating.
5. *Variegation.*—Cream colored, irregularly variegated leaf margin, near 4C to 4D, surrounding a darker green lamina.
6. *Color.*—Young leaf upper surface near 143A. Young leaf under surface near 138B to 138C. Mature leaf upper surface near 137A. Mature leaf under surface near 138B. Upper surface mid-rib near 11D. Under surface mid-rib near 154D. Petiole color near 144A.
7. *Texture.*—Smooth and glabrous, slightly glossy.
8. *Veination.*—Pinnate veination as is typical of *Ficus benjamina* with single mid-rib vein running from petiole to leaf apex.
9. *Serration.*—None.
10. *Stipules.*—Light green pointed sheaths with a trace of reddish brown; quickly withers, exfoliates and falls away as the new leaf emerges.
11. *Auricle.*—Absent.
12. *Petiole.*—About 10 mm long.

D. Wood:

1. *New shoots.*—Color — Light green to greenish brown.
2. *Old wood.*—Color — Brown.

NOTE: To date, and under conditions described herein, the new variety has not borne flowers or fruit.

3. *Temperature range.*—To 0° C.
4. *Preferred growing conditions.*—20° C. to 32° C., 5000 fc.

I claim:

1. A new and distinct cultivar of *Ficus benjamina* plant named 'Bushy King', substantially as illustrated and described, particularly characterized by short internode spacing and bushy, compact growth habit.

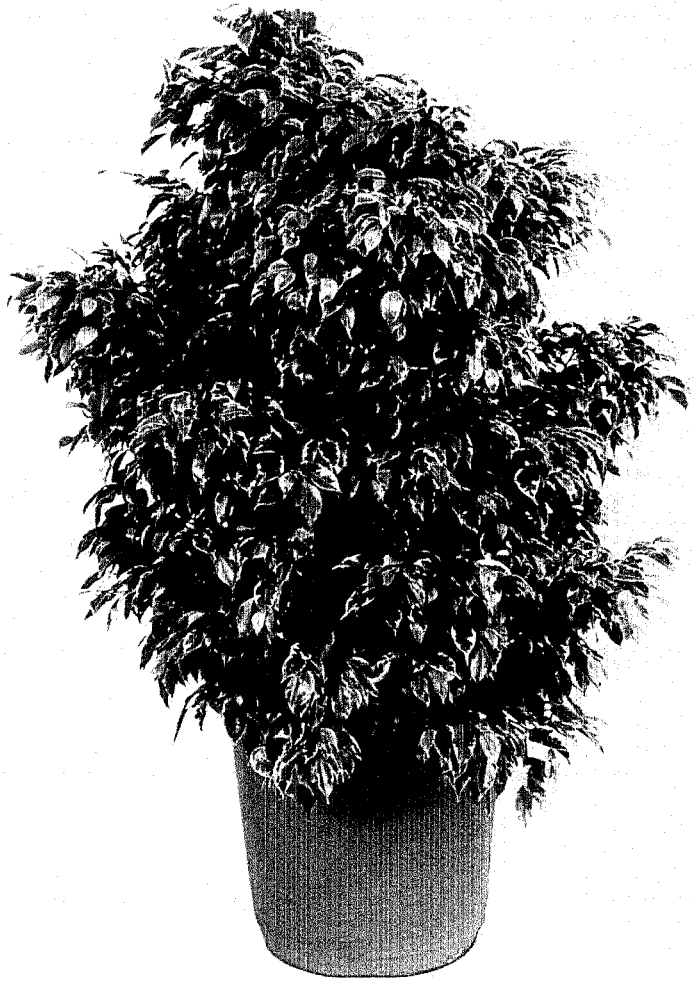

* * * * *